(12) United States Patent
Jones et al.

(10) Patent No.: US 10,470,887 B2
(45) Date of Patent: Nov. 12, 2019

(54) MODIFICATION OF THE SURFACE TOPOGRAPHY OF CARTILAGE GRAFTS FOR JOINT RECONSTRUCTION

(71) Applicant: Institute of Orthopedic Research & Education, Houston, TX (US)

(72) Inventors: Hugh Jones, Manvel, TX (US); Philip C. Noble, Houston, TX (US)

(73) Assignee: Institute of Orthopedic Research & Education, Houston, TX (US)

( * ) Notice: Subject to any disclaimer, the term of this patent is extended or adjusted under 35 U.S.C. 154(b) by 0 days.

(21) Appl. No.: 15/249,176

(22) Filed: Aug. 26, 2016

(65) Prior Publication Data

US 2017/0056182 A1    Mar. 2, 2017

Related U.S. Application Data

(60) Provisional application No. 62/210,529, filed on Aug. 27, 2015.

(51) Int. Cl.
*A61F 2/30* (2006.01)
*A61F 2/38* (2006.01)
*A61F 2/28* (2006.01)

(52) U.S. Cl.
CPC ............ *A61F 2/30756* (2013.01); *A61F 2/28* (2013.01); *A61F 2/30942* (2013.01); *A61F 2002/2839* (2013.01)

(58) Field of Classification Search
CPC .. A61F 2002/30751; A61F 2002/30752; A61F 2002/30754; A61F 2/30756; A61F 2002/30759; A61F 2002/30764; A61F 2/38; A61F 2/3859; A61F 2/3872; A61F 2/389
See application file for complete search history.

(56) References Cited

U.S. PATENT DOCUMENTS

| 6,454,811 B1* | 9/2002 | Sherwood ................. A61F 2/28 623/23.72 |
|---|---|---|
| 8,483,863 B1 | 7/2013 | Knox et al. |
| 2002/0082704 A1 | 6/2002 | Cerundolo |

(Continued)

OTHER PUBLICATIONS

International Search Report and Written Opinion dated Dec. 23, 2016 for corresponding International Patent Application No. PCT/US16/49098, (9 pgs.)
American Association of Tissue Banks, 2007 Annual Survey Results for AATB-Accredited Tissue Banks in the United States, 2010, (41 pgs.).
American Association of Tissue Banks, Standards for Tissue Banking, 2012, 13th Edition, (137 pgs.).

(Continued)

*Primary Examiner* — Alvin J Stewart
(74) *Attorney, Agent, or Firm* — Jonathan M. Pierce; Porter Hedges LLP (57) ABSTRACT

Herein disclosed is a tissue supplied in a configuration pre-shaped to the topography of the recipient surface for covering defects in the articulating surfaces of bones. Also discussed herein is a method of preparing a graft for reconstruction of a defect in an articular surface of a bone comprising determining the topography of the native articular surface and the corresponding underside of the cartilage layer; fabricating a pair of mating surfaces having the topography of the native articular surface and the underside of the cartilage layer; harvesting a cartilage graft from a cadaveric donor; and placing said graft between the mating surfaces and subjecting said graft to sufficient pressure for a sufficient duration to cause it to change shape to that of the deforming surfaces.

15 Claims, 5 Drawing Sheets

(56) References Cited

U.S. PATENT DOCUMENTS

| | | | |
|---|---|---|---|
| 2003/0055502 A1* | 3/2003 | Lang | A61F 2/30756 623/16.11 |
| 2003/0114936 A1* | 6/2003 | Sherwood | A61F 2/28 623/23.58 |
| 2004/0236424 A1* | 11/2004 | Berez | A61B 5/1076 623/14.12 |
| 2005/0222687 A1* | 10/2005 | Vunjak-Novakovic | A61F 2/28 623/23.63 |
| 2007/0129809 A1* | 6/2007 | Meridew | A61F 2/30721 623/22.32 |
| 2007/0233264 A1 | 10/2007 | Nycz et al. | |
| 2008/0077251 A1* | 3/2008 | Chen | A01N 1/02 623/23.72 |
| 2008/0262616 A1* | 10/2008 | McKay | A61B 17/1635 623/14.12 |
| 2008/0306608 A1* | 12/2008 | Nycz | A61B 6/481 623/23.57 |
| 2009/0043398 A1* | 2/2009 | Yakimicki | A61F 2/3094 623/23.51 |
| 2009/0209962 A1 | 8/2009 | Jamali | |
| 2010/0049322 A1* | 2/2010 | McKay | A61F 2/30756 623/16.11 |
| 2010/0256692 A1 | 10/2010 | Kang et al. | |
| 2012/0095469 A1* | 4/2012 | Meridew | A61B 17/1604 606/80 |
| 2013/0096680 A1 | 4/2013 | Ribeiro et al. | |
| 2015/0105696 A1 | 4/2015 | Litke et al. | |
| 2015/0351916 A1* | 12/2015 | Kosarek | A61F 2/30942 600/407 |
| 2016/0038291 A1* | 2/2016 | Netravali | A61B 17/17 606/86 R |
| 2017/0056181 A1* | 3/2017 | Rosenwasser | A61F 2/28 |
| 2017/0172747 A1* | 6/2017 | Bake | A61F 2/30756 |
| 2017/0333597 A1* | 11/2017 | Bhumiratana | A61L 27/3612 |
| 2018/0104062 A1* | 4/2018 | Chen | A61B 17/1604 |

OTHER PUBLICATIONS

Alford et al., "Cartilage Restoration, Part 1: Basic Science, Historical Perspective, Patient Evaluation, and Treatment Options", The American Journal of Sports Medicine, vol. 33, No. 2 , 2005, (12 pgs.).

Capeci et al.; "Osteochondral Allografts: Applications in Treating Articular Cartilage Defects in the Knee", Bull Hosp. Jt. Dis., 2013, (pp. 60-67).

Gortz et al. "Allografts in Articular Cartilage Repair", The Journal of Bone & Joint Surgery, JBJS.org, vol. 88-A, No. 6, Jun. 2006 (pp. 1374-1384).

Khanna et al., "Hip Technologies: Cartilage restoration of the hip using fresh osteochondral allograft", The Bone & Joint Journal, vol. 6, No. 11, Nov. 2014, (pp. 11-16).

Koh et al., "The Effect of Graft Height Mismatch on Contact Pressure Following Osteochonral Grafting, A Biomechanical Study", The American Journal of Sports Medicine, vol. 32, No. 2, 2004 ((pp. 317-320).

Martino, et al., "Chitosan: A versatile biopolymer for orthopedic tissue-engineering", Elsevier Ltd., Biomaterials 26 (2005), (pp. 5983-5990).

Qi et al., "Preparation and antibacterial activity of chitosan nanoparticles", Elsevier Ltd., Carbohydrate Research 339 (2004), (pp. 2693-2700).

Rinaudo, Chitin and Chitosan: Properties and applications, Elsevier Ltd.,Prog. Polym. Sci. 31 (2006), (pp. 603-632).

Skendzel, "Arthroscopic Glenoid Osteochondral Allograft Reconstruction Without Subcapularis Takedown: Technique and Literature Review", Arthroscopy: The Journal of Arthoroscopic and Related Surgery, vol. 27, No. 1, Jan. 2011, (pp. 129-135).

PCT International Preliminary Report on Patentability dated Mar. 8, 2018 for corresponding WO Patent Application No. PCT/US2016/049098, 6 pages.

* cited by examiner

MODIFICATION OF THE SURFACE TOPOGRAPHY OF CARTILAGE GRAFTS FOR JOINT RECONSTRUCTION

CROSS-REFERENCE TO RELATED APPLICATIONS

This application claims the benefit under 35 U.S.C. § 119(e) of U.S. Provisional Patent Application No. 62/210,529, filed Aug. 27, 2015, the disclosure of which is hereby incorporated herein by reference in its entirety.

STATEMENT REGARDING FEDERALLY SPONSORED RESEARCH OR DEVELOPMENT

Not Applicable.

FIELD OF THE DISCLOSURE

The present disclosure relates generally to joint reconstruction. More particularly, this disclosure describes a method to modify the surface topography of cartilage grafts obtained from a donor site for treatment of defects in the surface of a joint.

BACKGROUND

Articular cartilage is a highly specialized tissue that covers the surfaces of long bones to allow almost frictionless motion under large loads. In the healthy skeleton, this articulating function allows bones to change their relative angular relationship about a joint, as in the hip and the knee joints. This function of joints occurs painlessly and virtually without additional effort due to the low friction of mating joint surfaces which arises from the properties of the synovial fluid within the joint, and the smooth topography of the cartilage surfaces.

Although cartilage contains its own specialized cells (chondrocytes), it has limited ability to repair injuries, which may range from localized tears, to focal areas of loss of coverage of the underlying bone, to degenerative conditions, such as osteo- and rheumatoid arthritis in which the entire cartilage layer and underlying (subchondral) bone can be affected. Generalized or degenerative conditions, most commonly osteoarthritis, are frequently treated with total joint replacement in which the cartilage surface and underlying bone are completely replaced with artificial materials that articulate with minimal friction. In cases where the area of cartilage loss or mechanical damage is limited to a focal location within otherwise normal cartilage, the treatment of choice is to replace the damaged tissue with a graft taken from some other site within the patient's joint (e.g. the trochlea of the distal femur) or from an anatomically similar location in a bone obtained from, e.g., an animal donor (xenograft) or more preferably from a human donor. Grafts harvested from the patient's own body are termed "autografts", while grafts harvested from human cadavers are termed "allografts". Cartilage grafts are typically harvested in the form of a cylindrical core consisting of a surface layer of cartilage attached to a layer of subchondral bone which is in continuity with the spongy (cancellous) bone deep to the joint surface. These composite (osteochondral) grafts are machined (drilled) from sites within the joint (the "donor site"), and are designed to accurately match the dimensions of holes machined (drilled or cored) into the patient's joint at the site of cartilage damage (the "recipient site").

The sites available for harvesting of cartilage grafts within the body are limited and present a risk of secondary oeteoarthritis due to the loss of the weight-bearing area of the native joint. In addition, as these donor sites are typically located within the distal femur at the periphery of the articular surface, the diameter of autografts harvested in this manner is typically limited to 10 mm. Because of these limitations, there is rapidly growing interest in the use of osteo-chondral grafts derived from cadaveric specimens, in which the cartilage cells have been kept alive for transplantation to the host recipient site.

Numerous published articles have documented favorable clinical outcomes after treatment of cartilage defects with osteochondral allografts, with few cases of immunogenic reactions or transmission of disease when the guidelines of the American Association of Tissue Bank have been observed. Despite these favorable results, practical obstacles impede the use of live allografts and their efficacy in the reconstruction of chondral surfaces. The Musculoskeletal Transplant Foundation has reported that nearly 13% of donor grafts surpass their expiration date and are disposed of before they can be utilized. This waste of donor tissue arises from two limiting factors: (i) the viability period of the graft, and (ii), difficulties in selecting a graft of the appropriate size and shape to match the anatomy of the recipient.

After harvesting a live articular specimen (e.g. a femoral condyle) and placing it in a bath of nutrient solution, the cell population within the cartilage gradually dies, causing deterioration of the load-bearing properties of the tissue. After approximately 4 weeks, the graft is degraded to such an extent that it becomes unusable for transplantation. It may be assumed that a period of two weeks is required to harvest, process, test, and catalogue the donated tissue. This means that the time available to then match the size and shape of the harvested bone to a patient and then to obtain the donor specimen and perform the implantation procedure is only a period of approximately two weeks.

A further consideration is the correspondence between the surface geometry (i.e. topography) of the graft that is implanted at surgery versus the surface geometry of the original chondral surface at the recipient site. This is of critical significance to the success of the grafting procedure. If the surface of the implanted plug protrudes above the original articular surface, the cartilage surface of the graft will be subject to excessive stress during weight-bearing and articulation and will not survive. This situation arises (i) when the curvature of the chondral layer of the graft is smaller than the original surface (i.e. the original cartilage is flatter than the plug), and (ii) when the hole machined in the host bone to receive the transplanted core is too shallow or is not correctly aligned with respect to the surrounding surface. Conversely, if the surface of the implanted graft is lower than that of the original articular surface, the cartilage immediately surrounding the graft will be subject to higher stresses, leading to damage during weight-bearing and articulation. This configuration is present when the surface of the graft is lower than the matching edge of the surrounding cartilage at some points at the graft periphery, or when the edge of the graft is aligned with the surface of the joint at the periphery but undergoes less elevation at the center of the graft compared to the original joint surface. In either situation enlargement of the area of cartilage degeneration may occur over a larger area than the original cartilage defect, and thus failure of the procedure to restore the health of the joint. Typically, this situation arises when the curvature of the chondral layer of the graft is larger than the original surface (i.e. the surface of the graft is flatter than the surrounding joint surface), or the hole drilled in the host bone to receive the transplanted core is too deep or is not correctly aligned with respect to the surrounding surface. Clinical experience has shown that a surface mismatch of less than approximately 0.5 mm is acceptable without adversely affecting the success of the procedure.

As each joint is unique in terms of the geometry of its articulating surfaces, any graft derived from another bone will have areas of imperfect topographic match, even if implanted perfectly. As the curvature of articular surfaces is approximately proportional to the gross dimensions (i.e. the overall width and depth) of the joint surface, the chances of obtaining an allograft that will yield a graft of acceptable curvature increase if the allograft is of approximately the same size as the patient's joint. However, this requirement significantly limits the number of allografts available to provide grafts for any individual patient with an articular defect that requires cartilage transplantation.

The current practice for selecting articular specimens to provide a cartilage graft for treatment of a specific recipient lesion simply involves matching the overall dimensions of the joints of donors and recipients, without regard to the topographies of the cartilage surfaces of the donor and recipient joints. For example, if a graft is requested for a patient with a defect of the medial femoral condyle (MFC) of the right knee, measurements will be taken of the length and width of the patient's right femoral condyle on knee radiographs. The tissue bank will then match these radiographic dimensions with the population of medial condylar allografts that it has on-hand using a tolerance of ±2 mm for the matching procedure. When this method of matching allografts to patients is performed, many requests for bony tissue go unfulfilled, increasing the wait-time for patients. Furthermore, the use of linear dimensions for donor/patient matching ignores the variation in curvature amongst condyles of a given size. This leads to significant challenges in achieving acceptable host-recipient matches during surgery and potential functional problems with graft incorporation and cartilage viability post-operatively. Therefore it is apparent that there exists a need to reduce waste, patient wait-time, and improve function through more efficient selection of donor graft sources using matching methods based on surface curvature of the donor and recipient joints.

It is the object of the current disclosure to provide a method and system in which donor articular cartilage surface curvatures are precisely matched to the patient's natural curvature while reducing wait-time and minimizing waste. This method and system will allow a surgeon to essentially order a graft of any given curvature to repair a cartilage defect and to receive said graft in a timely manner on a pre-determined date.

SUMMARY

Herein disclosed is a tissue for covering defects in a recipient surface of the articulating surfaces of bones, wherein said tissue is supplied in a configuration pre-shaped to the topography of the recipient surface. In an embodiment, such tissue comprises a cartilage tissue graft supplied in a configuration pre-shaped to the original topography of the recipient surface. In an embodiment, the cartilage tissue graft consists of a layer of living cartilage attached to a layer of subchondral bone and is supplied in a configuration pre-shaped to the topography of the recipient surface.

Also disclosed herein is an osteochondral plug consisting of a layer of living cartilage pre-shaped to the topography of a recipient surface; a cylindrical segment formed from cancellous bone or a bone substitute; and, optionally, an intermediate layer of subchondral bone.

Further discussed is a method of preparing a graft for reconstruction of a defect in an articular surface of a bone comprising: removing cartilage at the site of the defect to expose subchondral bone; cutting a sheet of donor cartilage to form a graft of appropriate size and shape to fit the dimensions of the exposed bone; attaching the graft to the exposed bone; and deforming the graft to match the topography of the underlying bony surface.

In an embodiment, the method comprises machining the exposed bone at the site of the defect to match the topography of a pre-formed cartilage graft and attaching the graft to the exposed and machined bone.

Discussed herein is a method of preparing a graft for reconstruction of a defect in an articular surface of a bone comprising: exposing subchondral bone at the site of an articular defect; removing bone at the site of the defect to form a cavity within the underlying bone; placing bone or bone substitute within the cavity; forming the uppermost surface of the bone or bone substitute within the cavity to match the topography of a pre-formed cartilage graft; and attaching the graft to the exposed bone.

In an embodiment, the method comprises forming the uppermost surface of the bone or bone substitute within the cavity to match the topography of a pre-formed osteochondral graft consisting of a layer of cartilage and its native sub-chondral bone; cutting the periphery of the osteochondral graft to fit the dimensions of the exposed chondral defect; and attaching the graft to the uppermost surface of the bone or bone substitute.

Also disclosed is a method of preparing a graft for reconstruction of a defect in an articular surface of a bone comprising: determining the topography of the native articular surface and the corresponding underside of the cartilage layer; fabricating a pair of mating surfaces having the topography of the native articular surface and the underside of the cartilage layer; harvesting a cartilage graft from a cadaveric donor; and placing said graft between the mating surfaces and subjecting said graft to sufficient pressure for a sufficient duration to cause it to change shape to that of the deforming surfaces. In various embodiments, the graft is held in such deformed configuration for a sufficient time so that when the deforming load is removed, the graft substantially maintains the deformed shape for a duration sufficient to allow its implantation within the recipient site.

In an embodiment, the cartilage graft consists of a bilayer of cartilage attached to its native sub-chondral bone. In an embodiment, the cartilage graft consists of a layer of cartilage attached to its native sub-chondral bone and underlying cancellous bone. In an embodiment, the layer of subchondral bone has been modified to facilitate the change in shape occurring during the deformation process. In an embodiment, one or more grooves are formed in the underside of the subchondral bone to facilitate the change in shape occurring during the deformation process.

Further discussed herein is a method of preparing a graft for reconstruction of a defect in an articular surface of a bone comprising obtaining magnetic resonance images of said articular surface and the underlying bone in the vicinity of the defect; reconstructing the magnetic resonance images to generate a three-dimensional representation of the topography of the articular surface and the underlying bone in the vicinity of the defect; selecting target topography of the articular surface after implantation of a cartilage graft; fabricating a pair of mating surfaces having the target topography of the articular surface and the underside of the cartilage layer; harvesting a cartilage graft from a cadaveric donor; placing said graft between the mating surfaces and subjecting said graft to sufficient pressure for a sufficient duration to cause it to adopt the shape of the deforming surfaces, even when the deforming force is removed; and attaching the deformed graft to a bone or bone substitute.

The foregoing has outlined rather broadly the features and technical advantages of the invention in order that the detailed description of the invention that follows may be better understood. Additional features and advantages of the invention that form the subject of the claims of the invention will be described also. It should be appreciated by those skilled in the art that the conception and the specific embodiments disclosed may be readily utilized as a basis for modifying or designing other structures to accomplish the same purposes of the invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present disclosure, and the advantages thereof, reference is now made to the following description to be taken in conjunction with the accompanying drawings describing specific embodiments of the disclosure, wherein.

DETAILED DESCRIPTION

Overview. The disclosure herein is applicable to the repair of articular cartilage defects. Briefly, this method and system provides a means to reshape harvested cartilaginous tissue to a specified target curvature while maintaining cellular viability. After the processed tissue has been permanently deformed, the customized graft will be fixed to a pre-prepped allograft bone plug and transplanted into the recipient using traditional techniques and instrumentation for osteo-chondral transplantation.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the disclosure, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements and components comprising one unit and elements or components that comprise more than one unit unless specifically stated otherwise.

For the purposes of illustration, the application of the disclosure will be discussed for treatment of cartilage defects of the knee joint. However, it will be recognized that the systems and methods may also be applied to other joints of the body, including the hip, shoulder, or ankle joints, joints of the wrist, hand, foot or spine, or any other joints. Moreover, the cartilage defects treated using the inventive method may be present in any mammal, in addition to humans.

Herein disclosed is a tissue for covering defects in a recipient surface of the articulating surfaces of bones, wherein the tissue is supplied in a configuration pre-shaped to the topography of the recipient surface. In some embodiments, the issue comprises a cartilage tissue graft supplied in a configuration pre-shaped to the topography of the recipient surface. In some cases, the cartilage tissue graft comprises a layer of living cartilage attached to a layer of bony tissue where the configuration of the graft is supplied pre-shaped to the topography of the recipient surface.

Herein also disclosed is an osteochondral plug comprising a layer of living cartilage pre-shaped to the topography of a recipient surface; and a cylindrical plug formed from one or more of the following: (i) cancellous bone, (ii) compacted particles of morselized bone, and (iii) a bone graft substitute. In an embodiment, the osteochondral plug comprises a layer of the bony tissue that is originally attached to the cartilage constituting the cartilage layer.

Further discussed is a method of preparing a graft for reconstruction of a defect in an articular surface of a bone comprising: removing cartilage at the site of the defect to expose underlying bone; cutting a sheet of donor cartilage to form a graft of appropriate size and shape to fit the dimensions of the exposed bone; deforming the graft to match the topography of the underlying bony surface, and attaching the graft to the exposed bone.

In an embodiment, the method comprises machining the exposed bone at the site of the defect to match the topography of a pre-formed cartilage graft and attaching the graft to the exposed and machined bone.

Discussed herein is a method of preparing a graft for reconstruction of a defect in an articular surface of a bone comprising: exposing subchondral bone or calcified cartilage bone at the site of an articular defect; removing bone at the site of the defect to form a cavity within the underlying bone; placing bone or bone substitute within the cavity; forming the uppermost surface of the bone or bone substitute within the cavity to match the topography of a pre-formed cartilage graft; and attaching the graft to the prepared surface of the bone or bone substitute within the cavity.

In an embodiment, the method comprises forming the uppermost surface of the bone or bone substitute within the cavity to match the topography of a pre-formed osteochondral graft consisting of a layer of cartilage and its native calcified cartilage with or without a layer of sub-chondral bone; cutting the periphery of the osteochondral graft to fit the dimensions of the exposed chondral defect; and attaching the graft to the uppermost surface of the bone or bone substitute.

Discussed herein is a method of preparing a graft for reconstruction of a defect in an articular surface of a bone comprising: determining the topography of the native articular surface and the corresponding underside of the cartilage layer; fabricating a pair of mating surfaces having the topography of the native articular surface and the underside of the cartilage layer; harvesting a cartilage graft from a cadaveric donor; and placing the graft between the mating surfaces and subjecting the graft to sufficient pressure for a sufficient duration to cause it to change shape to that of the deforming surfaces and to maintain that shape to a substantial degree when the mating surfaces are removed.

In an embodiment, the cartilage graft consists of a construct consisting of a layer of uncalcified cartilage attached to its native layer of calcified cartilage. In an embodiment, the layer of calcified cartilage has been modified to facilitate the change in shape occurring during the deformation process. In an embodiment, the cartilage graft consists of a layer of cartilage attached to its native sub-chondral bone or a layer of bone graft or bone graft substitute. In an embodiment, the layer of sub-chondral bone has been modified to facilitate the change in shape occurring during the deformation process. In an embodiment, one or more grooves are formed in the underside of the subchondral bone to facilitate the change in shape occurring during the deformation process.

Discussed herein is a method of preparing a graft for reconstruction of a defect in an articular surface of a bone comprising: obtaining magnetic resonance images of the articular surface and the underlying bone in the vicinity of the defect; reconstructing the magnetic resonance images to generate a three-dimensional representation of the topography of the articular surface and the underlying bone in the vicinity of the defect; selecting a target topography of the articular surface to be achieved through implantation of the cartilage graft; fabricating a pair of mating surfaces having the target topography of the articular surface and the underside of the cartilage layer; harvesting a cartilage graft from a cadaveric donor; placing the graft between the mating surfaces and subjecting the graft to sufficient pressure for a sufficient duration to cause it to change shape to that of the deforming surfaces; and attaching the deformed graft to a bone or bone substitute.

Cartilage and Subchondral Plate Reshaping. A pilot study was conducted to explore the feasibility of harvesting and mechanically deforming a living cartilage graft with an intact subchondral bone. For the purposes of this disclosure, the term "subchondral bone" is intended to include the layer of calcified cartilage below the tide mark and the adjacent non-porous layer of bone, alternatively referred to as the "subchondral plate". Our goal was to deform the graft to provide an exact match to the geometry of a recipient site while maintaining the viability of the tissue. Bovine tarsal joints were obtained from a local abattoir at the time of slaughter and dissected to expose both condyles. The radii of curvature of the tarsal condyles differ when comparing the lateral ($\approx$10 mm) to medial sides ($\approx$26 mm). The three-dimensional surface topography of each tarsal condyle was reconstructed by first measuring the spatial coordinates of the cartilage surfaces with a high-resolution laser scanner (Farro Technologies, Inc. Lake Mary Fla. USA) with an accuracy of 0.035 mm. The sampled point-cloud data was then reconstructed using reverse engineering software (GeoMagic Rock Hill, S.C. USA).

Figure 1:
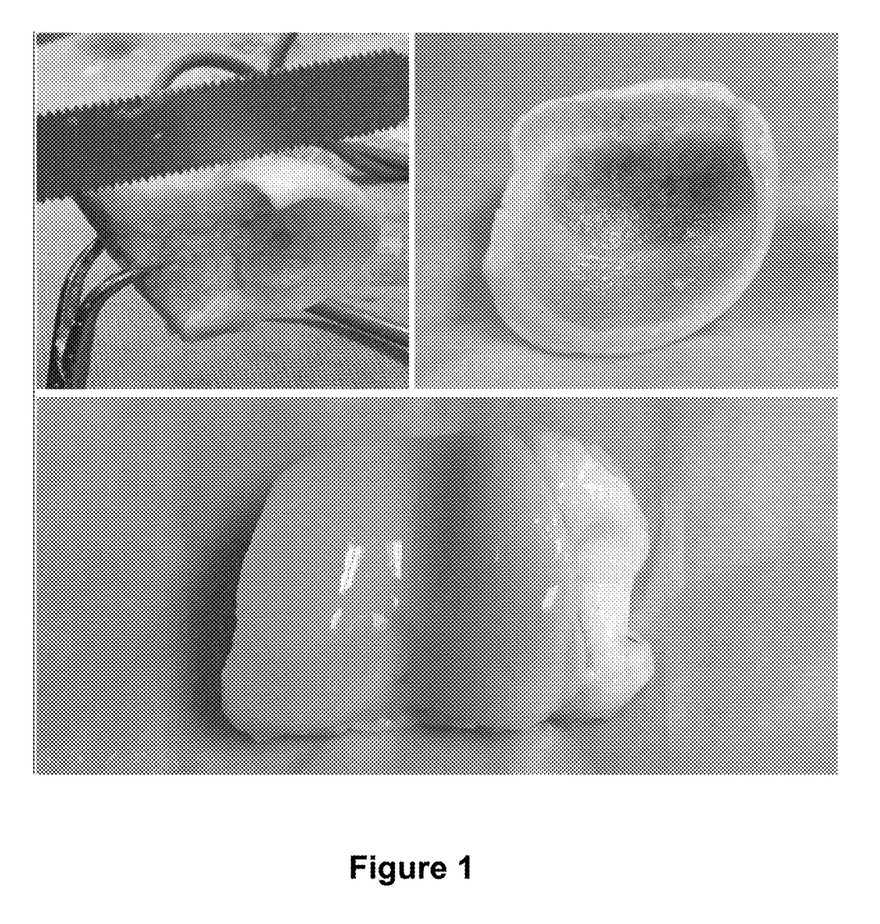
FIG. 1 illustrates harvested bovine tarsal condyles, according to an embodiment of this disclosure.

The cancellous bone was removed from the underside of the joint surface using a surgical drill under a saline cooling drip (FIG. 1). This left the subchondral plate intact and in continuity with the calcified and non-calcified layers of the articular cartilage (thickness$\approx$2-3 mm).

Figure 2:
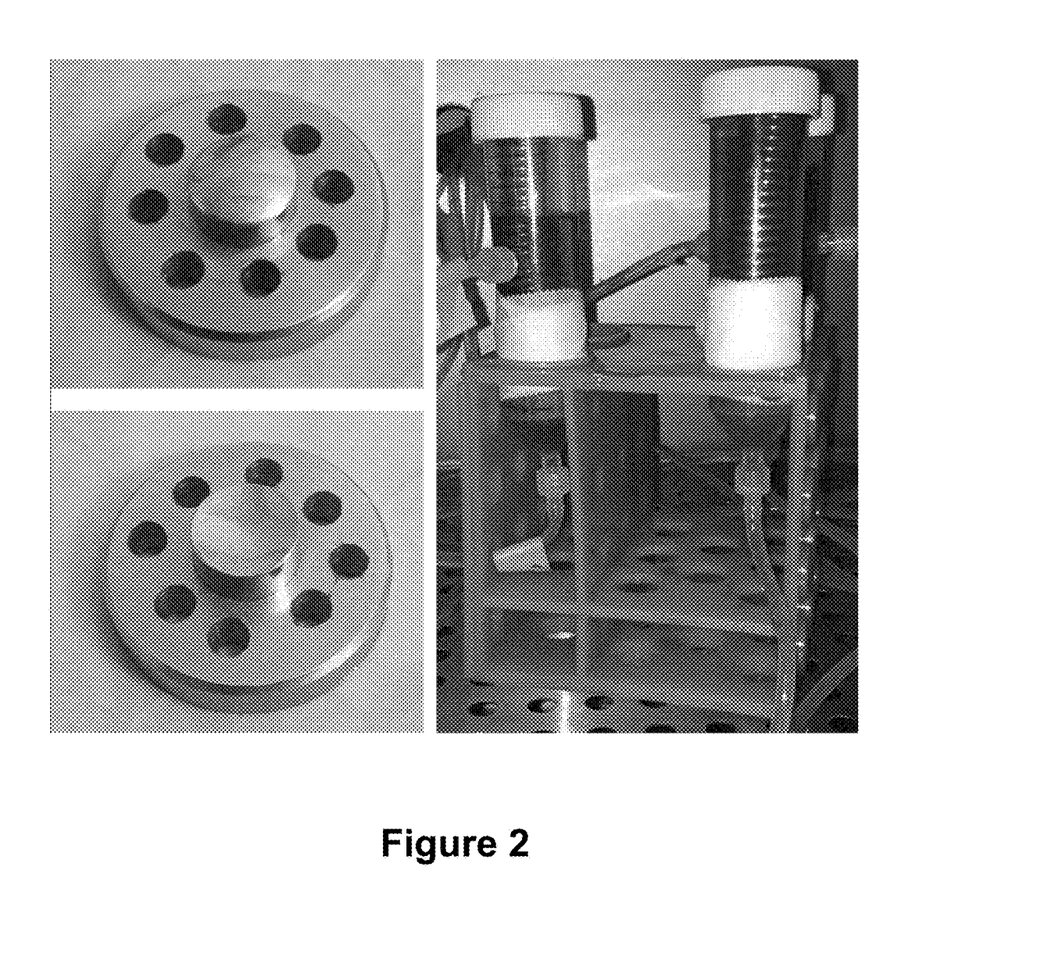
FIG. 2 illustrates deformation molds and centrifuge tube specimen chambers in incubation, according to an embodiment of this disclosure.

The condyles were then separated and the medial specimens (donor) were statically cultured for 24 hours in 6 well plates to acclimate, during which time stainless steel molds of the target geometry (lateral condyle) were fabricated using a computer numerically controlled (CNC) milling machine using tooling paths obtained from the 3D reconstruction of the articular surface (FIG. 2). The specimens (loaded and an unloaded control) were trimmed, sandwiched between the fabricated molds, and inserted into centrifuge tubes (50 ml) outfitted with inlets connected to O2/CO2 permeable silicone tubing for media circulation via a peristaltic pump. Prior to assembly in the centrifuge tubes, five osteochondral shells were mechanically tested to determine their stiffness, yield point, and ultimate failure load. Briefly, the cartilage-subchondral shells were potted in a metal ring using casting resin (Smoothcast 300) at depth ⅓ from its end. The specimens were then mounted to a MTS machine upon which the pneumatic actuator was made to contact the free cartilage end creating a bending moment. The MTS actuator then applied an increasing compressive force at 1 mm/sec until failure. The specimens were found to have an average stiffness of 5.2±1.0 N/mm, a yield point of 19.5±2.6N, and an ultimate failure strength of 35±8N. A compressive spring was then selected to deliver a constant force (26.7 N) that fell within the plastic deformation zone of the specimens and assembled within the specimen chambers (FIG. 2).

Figure 3:
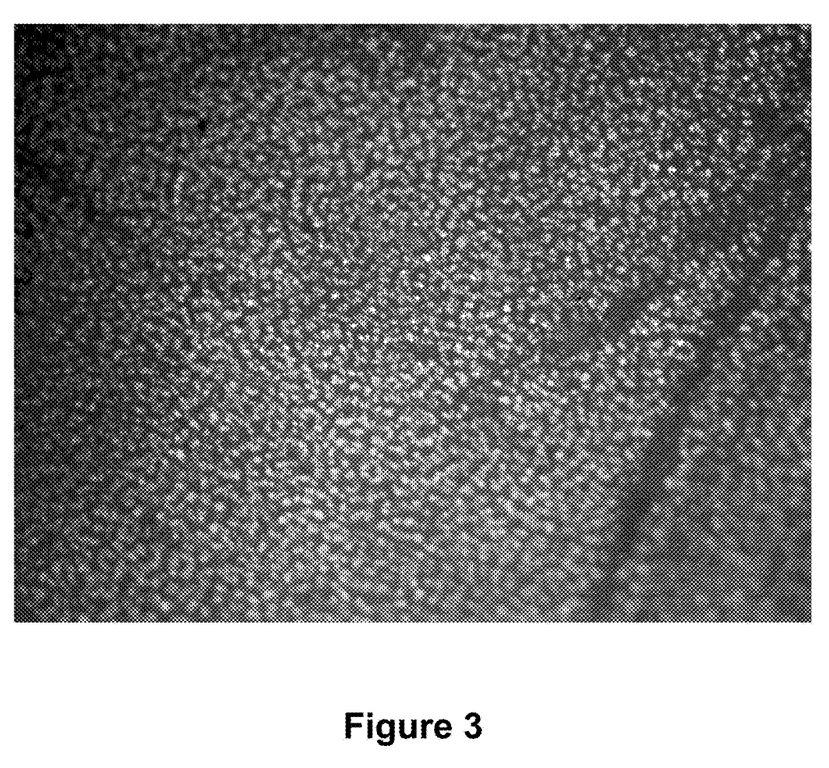
FIG. 3 illustrates live/dead staining at day 6, according to an embodiment of this disclosure.

The osteo-chondral specimens were assembled in the specimen chambers in contact with the compressed spring (load: 27N (6.0 lbs)), and incubated for six days in specialized media (Dulbecco's Modified Eagle Medium containing 10% fetal bovine serum, 3% antibiotic/antimycotic, 50 ug/ml ascorbic acid, and 40 ug/ml L-proline). After this period, the load was released and each specimen was allowed to relax in static culture for seven hours. Tissue samples taken from the periphery of each specimen underwent live/dead fluorescence staining for comparison to the unloaded static controls. No dead cells were detected in either group (FIG. 3). The experimental group was then prepared for transplantation.

Custom Allograft Transplantation. To maintain the prescribed curvature after implantation, the underlying bone structure should complement the new geometry without gaps between the subchondral plate and bone bed. To achieve this, we utilized compacted morselized bone coated with a chitosan gel base to act as a binder and molded the supporting bone composite to the cartilage shell.

Figure 4:
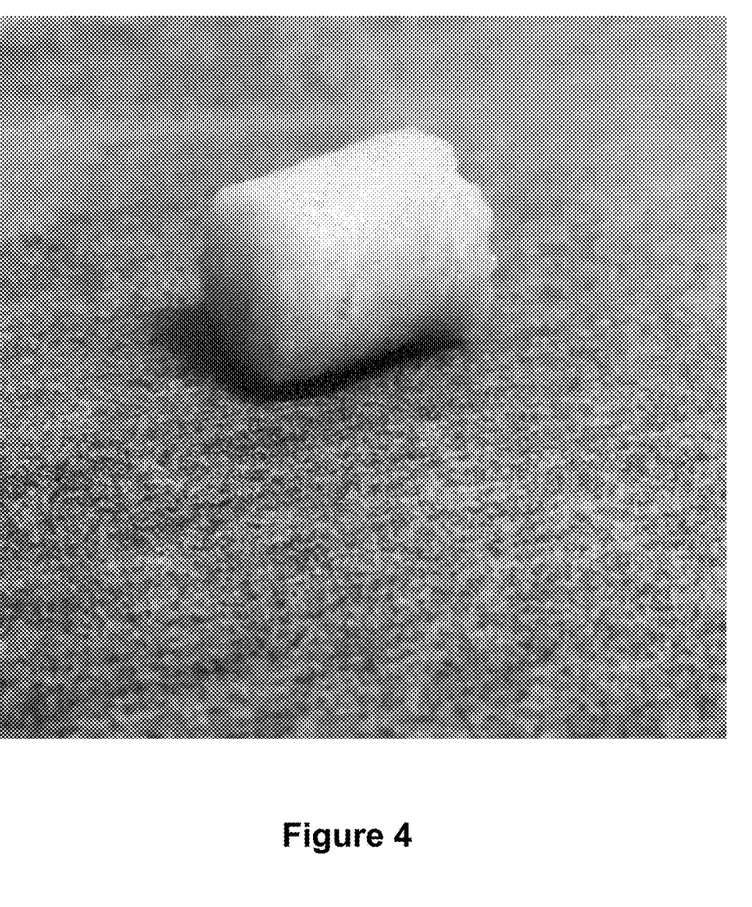
FIG. 4 illustrates solidified chitosan-morselized bone composite, according to an embodiment of this disclosure.

Chitosan is a natural polymer having unique properties. It has been studied as a biological scaffolding material and found to be inherently antimicrobial while promoting cell adhesion and migration. Chitosan is biodegradable at a controllable rate and is also pH responsive in that it is a gel at levels below 6.2 and a solid at higher pH levels. We exploited the pH responsiveness of this material by mixing it in gel form with morselized bone and compacting into a modified syringe that housed the reshaped cartilage shell. Phosphate buffered saline, having a pH of 7.4, was then flooded into the syringe sleeve and left until the chitosan solidified (FIG. 4). The syringe was then used to inject and seat the construct into the surgical bore of the recipient specimen. After seating of the graft in the defect site, 3D laser scans were taken of the cartilage surface with the graft in place. After reconstructing the scan data, we compared the topography of the joint surfaces in the original, intact state and after grafting. This was achieved by initially aligning the two surface models and then measuring the separation of the two cartilage surfaces in the vicinity of the graft and surrounding cartilage.

Figure 5:
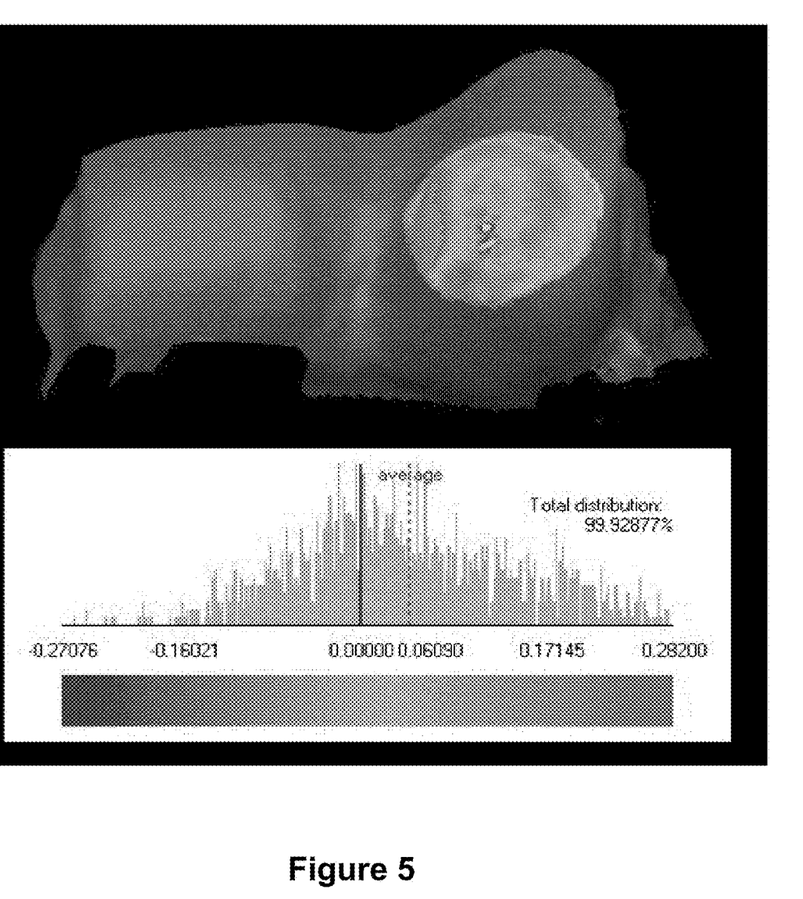
FIG. 5 illustrates laser scan model of bovine tarsal condyle, according to an embodiment of this disclosure.

Maps generated from these data (RapidForm GeoMagic Oak Hill, S.C.) displayed the spatial distribution of the error of reconstruction of the original articular surface. The average separation of the two surfaces was 61 µm of overcorrection (i.e., defect area proud to original surface) (FIG. 5), ranging from a minimum of −160 µm (new surface underfilled) to a maximum of +280 µm (new surface over-filled).

EXAMPLES

The following examples are included to demonstrate ways in which the present disclosure might be applied to the treatment on cartilage defects as they are encountered in any joint, but especially the major joints at the ends of the long bones of the skeleton, most frequently the knee, shoulder, ankle and hip joints. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

As outlined herein above, we propose that the utility of articular allografts be expanded by shaping cartilage grafts to match the topography of a specific recipient site. We further propose that this "reshaping" be achieved by deforming a graft between surfaces with a topography modeled from the geometry of the recipient joint surface. In the embodiment described above, the geometry of the deforming surfaces was determined by laser scanning the intact surface prior to creation of an experimental defect. In clinical application, these data would be obtained through any convenient, preferably non-invasive method, including imaging of the affected joint with magnetic resonance imaging (MRI) or computer tomography (CT). As the topography of the defect site will be distorted by the effects of pathology and/or previous surgery, the surface topography of the restored surface may be derived through a variety of methods, including interpolation of the articular surface surrounding the defect, imaging the contralateral intact joint surface and then mirroring the extracted data to match the geometry of the recipient site, or prediction of the target topography using an atlas of articular surfaces or through statistical shape modeling of the morphology of joint in question. After the target geometry has been defined and modeled, the surfaces used to shape the graft material may be fabricated from a bio-compatible/bio-tolerant material via CNC machining or other processes such as 3D printing or additive manufacturing.

The donor tissue that has been harvested and subjected to current tissue bank protocols will be prepped in a manner as described above to form cartilage-bone graft shells consisting of layers of cartilage and bony tissue and/or bone substitute and loaded into the deformation chamber. This chamber can consist of any culture vessel that will induce media agitation and allow gas exchange while delivering a compressive force sufficient to plastically deform the specimens without fracture. The cartilage-bone graft shells are incubated for approximately 6 days or until creep has ended.

In one embodiment, the preformed graft consists of a bilayer of cartilage and native subchondral bone which has been cut to match the dimensions of the defect site after removal of all loose or diseased cartilage to expose healthy, adherent tissue. As cells remaining within cancellous bone have immunologic potential, all cancellous bone is removed from the allograft, leaving a shell of approximately 5 mm in thickness. We have discovered that reliable fixation of allograft plugs in the recipient site requires a minimum plug length of at least 9-10 mm; so additional inert material must be bonded to the deformed shell to provide support and stable anchorage within the host tissue. In addition to acellular bone, there are numerous bone substitute materials that may be used to form a plug supporting the cartilage-bone composite graft. As discussed above, one choice of material for this purpose is a composite of chitosan, mixed with morselized bone derived from the donor. However other osteoinductive/osteoconductive materials having suitable mechanical properties can be used such as: lyophilized or demineralized bone morsels, polyglycolic acid (PLGA) and its stereo-isomers, hydroxyapatite (HA), etc. Whichever material is selected, it must be initially moldable to the subchondral plate and capable of forming a dowel plug.

Upon forming, the dowel plug is then ready for length matching and seating into the surgically prepped defect site. As mentioned, the rotational position and seating depth of the dowel plug are critical to the success of the inventive device. The cylindrical molding sleeve can be utilized to facilitate final positioning of the allograft by introducing a plunger to the articular side of the graft. The plunger can then be advanced until the correct graft height is reached, after which the bony side is cut flush with the sleeve end. The seating process by be facilitated by attaching a custom-fabricated flange to the sleeve with a shape that matches the contours of the joint surface, as determined from the MRI based CAD models. When the flange is placed congruent with the articular surface, the plunger will be further advanced until the construct is seated.

Typically, dowel type osteochondral allografts rely on press-fit fixation to stabilize the graft. Alternatively, fixation of the dowel-shaped graft may be augmented using sutures or bio-adhesives.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure.

What is claimed is:
1. A method of preparing a graft for reconstruction of a defect in an articular surface of a bone, comprising:
   removing cartilage at a site of an articular defect to expose bone;
   cutting a sheet of donor cartilage tissue to form a graft of appropriate size and shape to fit dimensions of the exposed bone;
   deforming the graft by placing said graft between mating surfaces of a mold to cause the graft to change shape to that of the mating surfaces and to maintain that shape to a substantial degree when the mating surfaces are removed; and attaching the deformed graft to the exposed bone.

2. The method of claim 1 comprising machining the exposed bone at the site of the articular defect to match a topography of the deformed graft and wherein the deformed graft is attached to the exposed and machined bone.

3. The method of claim 1 wherein the graft includes a bilayer having a layer of uncalcified cartilage attached to its native layer of calcified cartilage, or wherein the graft includes a bilayer of cartilage attached to its native subchondral bone.

4. The method of claim 3 comprising fixing the graft to a pre-prepped allograft bone plug, wherein the pre-prepped allograft bone plug is formed from one or more of cancellous bone, compacted particles of morselized bone, and a bone graft substitute.

5. A method of preparing a graft for reconstruction of a defect in an articular surface of a bone, comprising:
    exposing subchondral bone or calcified cartilage bone at a site of an articular defect;
    removing bone at the site of the articular defect to form a cavity within underlying bone;
    placing morselized bone or bone substitute within the cavity;
    pre-forming a cartilage graft by placing said cartilage graft between mating surfaces of a mold to cause the cartilage graft to change shape to that of the mating surfaces and to maintain that shape to a substantial degree when the mating surfaces are removed;
    forming the uppermost surface of the morselized bone or bone substitute within the cavity to match a topography of the pre-formed cartilage graft; and
    attaching the pre-formed cartilage graft to the surface of the morselized bone or bone substitute within the cavity.

6. The method of claim 5, comprising:
    forming an uppermost surface of the morselized bone or bone substitute within the cavity to match a topography of the pre-formed cartilage graft;
    cutting a periphery of the cartilage graft to fit dimensions of the exposed articular defect; and
    attaching the cartilage graft to the uppermost surface of the morselized bone or bone substitute.

7. The method of claim 5, wherein the cartilage graft includes a bilayer having a layer of uncalcified cartilage and its native layer of calcified cartilage.

8. The method of claim 7, wherein the cartilage graft further includes sub-chondral bone.

9. A method of preparing a graft for reconstruction of a defect in an articular surface of a bone, comprising:
    determining a target topography of the articular surface and corresponding underside;
    fabricating a pair of mating surfaces of a mold, the mating surfaces having the target topography of the articular surface and the corresponding underside;
    harvesting a cartilage graft from a cadaveric donor; and
    placing said cartilage graft between the mating surfaces of the mold; and
    subjecting said cartilage graft to sufficient pressure for a sufficient duration to cause said cartilage graft to change shape to that of the mating surfaces and to maintain that shape to a substantial degree when the mating surfaces are removed.

10. The method of claim 9, wherein said cartilage graft includes a bilayer having a layer of uncalcified cartilage attached to its native layer of calcified cartilage.

11. The method of claim 10, wherein the layer of calcified cartilage has been modified to facilitate the change in shape.

12. The method of claim 9, wherein said cartilage graft includes a bilayer of cartilage attached to its native subchondral bone.

13. The method of claim 12, wherein the layer of subchondral bone has been modified to facilitate the change in shape occurring during the deformation process.

14. The method of claim 9 comprising fixing said cartilage graft to a pre-prepped allograft bone plug, wherein the pre-prepped allograft bone plug is formed from one or more of cancellous bone, compacted particles of morselized bone, and a bone graft substitute.

15. A method of preparing a graft for reconstruction of a defect in an articular surface of a bone, comprising:
    obtaining magnetic resonance images of said articular surface and underlying bone in a vicinity of the defect;
    reconstructing magnetic resonance images to generate a three-dimensional representation of a topography of the articular surface and the underlying bone in the vicinity of the defect;
    selecting a target topography of the articular surface after implantation of a cartilage graft based on the three-dimensional representation of the topography of the articular surface and the bone in the vicinity of the defect;
    fabricating a pair of mating surfaces of a mold, the mating surfaces having the target topography of the articular surface and corresponding underside;
    harvesting the cartilage graft from a cadaveric donor;
    placing said cartilage graft between the mating surfaces of the mold;
    subjecting said cartilage graft to sufficient pressure for a sufficient duration to cause said cartilage graft to change shape to that of the mating surfaces and to maintain that shape to a substantial degree when the mating surfaces are removed; and
    attaching the cartilage graft removed from the mating surfaces to a bone or bone substitute.

* * * * *

UNITED STATES PATENT AND TRADEMARK OFFICE
CERTIFICATE OF CORRECTION

PATENT NO. : 10,470,887 B2
APPLICATION NO. : 15/249176
DATED : November 12, 2019
INVENTOR(S) : Hugh Jones and Philip C. Noble It is certified that error appears in the above-identified patent and that said Letters Patent is hereby corrected as shown below:

In the Claims

In Claim 13, Line 1, cancel "layer of"; Line 3, cancel "occuring during the deformation process".

Signed and Sealed this
Twenty-seventh Day of October, 2020

Andrei Iancu
*Director of the United States Patent and Trademark Office*